United States Patent
Ye et al.

(10) Patent No.: US 12,098,432 B2
(45) Date of Patent: Sep. 24, 2024

(54) MUTATION SITE OF IDEAL BRITTLE CULM MUTANT ibc IN RICE, CONTROLLING GENE IBC, AND USE THEREOF

(71) Applicants: HEFEI INSTITUTES OF PHYSICAL SCIENCE, CHINESE ACADEMY OF SCIENCES, Hefei (CN); WIN-ALL HI-TECH SEED CO., LTD., Hefei (CN)

(72) Inventors: Yafeng Ye, Hefei (CN); Binmei Liu, Hefei (CN); Conghe Zhang, Hefei (CN); Yuejin Wu, Hefei (CN); Liangzhi Tao, Hefei (CN); Zhi Yan, Hefei (CN); Libin He, Hefei (CN); Guangle Shen, Hefei (CN); Hui Wang, Hefei (CN); Yue Zhan, Hefei (CN)

(73) Assignees: HEFEI INSTITUTES OF PHYSICAL SCIENCE, CHINESE ACADEMY OF SCIENCES, Hefei (CN); WIN-ALL HI-TECH SEED CO., LTD., Hefei (CN)

( * ) Notice: Subject to any disclaimer, the term of this patent is extended or adjusted under 35 U.S.C. 154(b) by 0 days.

(21) Appl. No.: 18/574,729

(22) PCT Filed: May 16, 2022

(86) PCT No.: PCT/CN2022/092957
§ 371 (c)(1),
(2) Date: Dec. 27, 2023

(87) PCT Pub. No.: WO2023/029587
PCT Pub. Date: Mar. 9, 2023

(65) Prior Publication Data
US 2024/0240265 A1 Jul. 18, 2024

(30) Foreign Application Priority Data
Aug. 31, 2021 (CN) .......................... 202111013421.4

(51) Int. Cl.
*C12Q 1/6895* (2018.01)
*C12Q 1/686* (2018.01)
*G01N 27/447* (2006.01)

(52) U.S. Cl.
CPC .......... *C12Q 1/6895* (2013.01); *C12Q 1/686* (2013.01); *G01N 27/447* (2013.01); *C12Q 2600/13* (2013.01)

(58) Field of Classification Search
None
See application file for complete search history.

(56) References Cited

U.S. PATENT DOCUMENTS

2008/0313777 A1  12/2008  Dhugga et al.

FOREIGN PATENT DOCUMENTS

| CN | 110964733 A | 4/2020 |
| CN | 113862280 A | 12/2021 |

OTHER PUBLICATIONS

Xingliang Ma, et al., A Robust CRISPR/Cas9 System for Convenient, High-Efficiency Multiplex Genome Editing in Monocot and Dicot Plants, Molecular Plant, 2015, pp. 1274-1284, vol. 8.
Jiang Hong-Rui, et al., Identification and gene localization of a novel rice brittle culm mutant bc17, Acta Agronomica Sinica, 2021, pp. 71-79, vol. 47, No. 1.
(Continued)

*Primary Examiner* — Samuel C Woolwine
(74) *Attorney, Agent, or Firm* — Bayramoglu Law Offices LLC

(57) ABSTRACT

A mutation site of an ideal brittle culm mutant ibc in rice, a controlling gene IBC, and use thereof are provided. The controlling gene IBC has: (1) a nucleotide sequence shown in SEQ ID NO: 1 or SEQ ID NO: 2; or (2) a nucleotide sequence of a mutant, an allele, or a derivative generated by adding, substituting, inserting or deleting one or more
(Continued)

nucleotides. The present disclosure further provides an encoded protein of the controlling gene IBC, a recombinant construct, a recombinant host cell, a method for embrittling culms in a rice ripening stage by using the controlling gene IBC, and use thereof. In a mutant with allelic variation in the gene IBC and loss of gene editing function, culms exhibit a brittle culm phenotype at the late ripening stage, leaves are not brittle, yield traits are excellent, and other agronomic traits are not obviously changed.

1 Claim, 10 Drawing Sheets

Specification includes a Sequence Listing.

(56) References Cited

OTHER PUBLICATIONS

Hu Wei-Chen, et al., Progress on cell wall biosynthesis and regulation in grasses, Jiangsu J. of Agr. Sci., 2018, pp. 472-480, vol. 34, No. 2.
XM_015776685.1, Predicted: Oryza sativa Japonica Group protein trichome birefringence-like 28 (LOC4332508), mRNA, GenBank, 2016.
MH037020.1, Oryza sativa Japonica Group cultivar japonica xylan O-acetyltransferase 6 (XOAT6) mRNA, complete cds, GenBank, 2018.

MUTATION SITE OF IDEAL BRITTLE CULM MUTANT ibc IN RICE, CONTROLLING GENE IBC, AND USE THEREOF

CROSS REFERENCE TO THE RELATED APPLICATIONS

This application is the national phase entry of International Application No. PCT/CN2022/092957, filed on May 16, 2022, which is based upon and claims priority to Chinese Patent Application No. 202111013421.4, filed on Aug. 31, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBHZY019-PKG_Sequence_Listing.txt, created on 10/12/2023, and is 24,088 bytes in size.

TECHNICAL FIELD

The present disclosure relates to the field of biotechnology, and in particular to a mutation site of an ideal brittle culm mutant ibc in rice, a controlling gene IBC, and use thereof.

BACKGROUND

Rice (*Oryza sativa* L.) is one of the most important food crops in the world, and the mechanical strength of its culm is one of the important agronomic traits, which is directly related to the lodging resistance of rice plants, thus ultimately affecting the yield of rice. In another aspect, rice also produces a large amount of straw every year, which can be used for livestock feed, papermaking raw materials, building materials, biomass energy, organic fertilizer raw material and others. However, due to the anti-degradation barrier of straw biomass, it is very difficult for straw to return to the field and other comprehensive utilization. It is highly desirable to break through the bottleneck of comprehensive utilization of rice straw from the composition and structure of rice straw itself.

The mechanical strength of rice culms and their biomass anti-degradation barriers are determined by the secondary cell wall. The secondary cell wall is a cell wall layer that continues to accumulate on the inner side of the primary cell wall after specific cells stop growing. The secondary cell wall is essentially composed of cellulose, hemicellulose, and lignin. The change of each component will affect the structural changes of the secondary cell wall, thus affecting the mechanical strength of the plant. In rice, brittle culm mutants are important materials for studying the biosynthesis of the secondary cell wall in rice. Most of the reported brittle culm mutants eventually affect the thickening of the secondary cell wall due to the decrease in cellulose content. In recent years, researchers in China and other countries have cloned many key genes for controlling the synthesis of the secondary cell wall in rice. For example, OsCESA4, OsCESA7, and OsCESA9 encode the catalytic subunit of cellulose synthase in the secondary cell wall of rice. Their mutations will lead to changes in culm mechanical strength, exhibiting a brittle culm phenotype. Among them, OsCESA9 has mutated from aspartic acid to asparagine at amino acid 387, exhibiting a semi-dominant brittle culm phenotype. Specifically, for example, Chinese Patent CN110964733A discloses a rice semi-dominant brittle culm controlling gene SDBC1, but the rice culms and leaves expressed by the gene can be easily broken. In addition, there are the BC1 and BC12 genes that affect the assembly and arrangement of cellulose, the BC3 gene that affects the transport of cellulose synthase vesicles, the BC10 gene that affects the hemicellulose synthesis, and the CEF1 gene that regulates the synthesis of the secondary cell wall in rice. Research on these genes provides a new theory for the synthesis of secondary cell wall in rice, and these mutant materials provide new genetic resources for the efficient utilization of rice straw.

In order to realize the efficient comprehensive utilization of rice straw, in addition to changing the composition of rice culm, it is further necessary to take into account its yield-related traits. The efficient utilization of rice straw cannot be improved at the expense of rice yield. Although the changes in the cell wall composition of most rice brittle culm mutants have a very high potential for promoting efficient utilization of rice straw, the planting of rice brittle culm mutants faces lots of problems in the actual production process, for example, the leaves are easy to break, affecting the field operation; the culm is susceptible to lodging, affecting the final yield; and the like.

The ideal brittle culm rice suitable for large-scale planting and production needs to have the following characteristics: 1) excellent yield traits; 2) strong lodging resistance; 3) not brittle leaves; and 4) the culm becomes brittle at the late ripening stage.

SUMMARY

One of the technical problems to be solved by the present disclosure is that leaves of a rice brittle culm mutant in the prior art are easy to break, affecting the field operation. The present disclosure provides a mutation site of a rice ideal brittle culm mutant ibc that has unbreakable leaves and is non-lodging, a controlling gene IBC, an encoded protein of the controlling gene IBC, a recombinant construct of the controlling gene IBC, a recombinant host cell of the controlling gene IBC, a method for embrittling culms at the rice ripening stage by using the controlling gene IBC, and use of brittle culm rice or brittle straw as a raw material in a feed or fertilizer.

The present disclosure solves the above technical problem by the following technical means:

A mutation site of an ideal brittle culm mutant ibc in rice is provided. The mutation site of the ideal brittle culm mutant ibc in rice is a chromosomal segment inversion, and the chromosomal segment inversion is located on an LOC_Os03g18140 gene.

The LOC_Os03g18140 gene is a controlling gene IBC.

A controlling gene IBC of an ideal brittle culm mutant ibc in rice is provided. The controlling gene IBC has: (1) a nucleotide sequence shown in SEQ ID NO: 1 or SEQ ID NO: 2; or (2) a nucleotide sequence of a mutant, an allele, or a derivative generated by adding, substituting, inserting, or deleting one or more nucleotides.

Alternatively, the nucleotide sequence shown in SEQ ID NO: 2 can hybridize under rigorous conditions, and simultaneously encode a nucleotide sequence controlling a culm mechanical strength at the ripening stage of rice.

The rigorous conditions are as follows: a hybrid membrane is placed in a pre-hybridization buffer (0.25 mol/L sodium phosphate buffer, pH 7.2, and 7% sodium dodecyl sulfate (SDS)) and pre-hybridized at 65° C. for 30 min; the pre-hybridization buffer is discarded, a hybridization buffer (0.25 mol/L sodium phosphate buffer, pH 7.2, 7% SDS, and isotope-labeled nucleotide fragment) is added, and hybridization is performed at 65° C. for 16 h; the hybridization buffer is discarded, a stripping buffer I (20 mmol/L sodium phosphate buffer, pH 7.2, 0.1% SDS) is added, and the hybrid membrane is washed twice at 65° C. for 10-15 min each time; a stripping buffer II (10 mmol/L sodium phosphate buffer, pH 7.2, 0.1% SDS) is added, and the hybrid membrane is washed at 65° C. for 10-15 min.

The nucleotide sequence shown in SEQ ID NO: 1 relates to a promoter, a coding region, and a flanking region of the controlling gene IBC.

In the present disclosure, heavy ions are utilized to irradiate a Chinese *japonica* rice cultivar, *Oryza sativa* subsp. *japonica* cv. Wuyunjing 7 (WYJ7), to obtain an ideal brittle culm (ibc) mutant having no effect on yield-related agronomic traits including plant height, tiller number, grain number per spike, thousand-grain weight, and lodging resistance, and exhibiting a brittle culm phenotype in the straw at the late filling stage.

In the present disclosure, through the genetic analysis and population construction of an ibc mutant and the analysis of genetic behavior thereof, it is found that the brittle culm phenotype of the ibc mutant is recessively controlled by a single gene IBC after mutation.

The present disclosure has the following beneficial effects: In the present disclosure, a gene IBC for controlling the rice culm mechanical strength is isolated and identified by map-based cloning; the phenotypic analysis and genetic complementation experiment of materials demonstrate the functions of the gene IBC in the regulation of mechanical strength and cell wall components of rice culms, and the gene is successfully used to cultivate a brittle culm rice cultivar *Oryza sativa* subsp. *japonica* cv. Kefujing 7 adapted to large-scale production, truly solving the problem of rice straw treatment from the source of the cultivar.

The IBC encodes xylan acetyltransferase and plays an important role in the modification of secondary cell wall hemicellulose polysaccharides. In a mutant with allelic variation in IBC and loss of gene editing function, culms exhibit a brittle culm phenotype in the late ripening stage, leaves are not brittle, yield traits are excellent, and other agronomic traits are not obviously changed; in the harvest stage, field-harvested culms are easy to crush, crushing and culm returning are facilitated, and the culms are easy to crush into silage in feed processing and to chew by animals.

The gene IBC provides a theoretical basis and material and gene support for elucidating the genetic basis for the regulation of rice secondary cell wall synthesis at the molecular level in the future, and the breeding of environmentally friendly new rice cultivars based on molecular design.

A protein encoded by a controlling gene IBC of an ideal brittle culm mutant ibc in rice is provided. The protein encoded by the controlling gene IBC has: (1) an amino acid sequence shown in SEQ ID NO: 3; (2) an amino acid sequence different from the amino acid sequence shown in SEQ ID NO: 3 due to the substitution, deletion and/or insertion of one or more (for example, 1-25, 1-20, 1-15, 1-10, 1-5, and 1-3) amino acid residues; or (3) one selected from amino acid sequences with at least 70%, preferably at least 80%, more preferably at least 90%, particularly at least 95%, 98%, or 99% identity with the amino acid sequence shown in SEQ ID NO: 3; or (4) one selected from active fragments of the amino acid sequences shown in (1), (2), or (3).

A recombinant construct is provided. The recombinant construct contains a nucleotide sequence of the controlling gene IBC for culm mechanical strength at the rice ripening stage, and a vector used for the recombinant construct is a cloning vector or an expression vector for expressing the nucleotide.

A recombinant host cell is provided, including a host cell of the foregoing recombinant construct, and a polynucleotide sequence integrated with the gene IBC for controlling rice culm mechanical strength according to the present disclosure in a genome thereof. The host cell may be selected from plant or microbial cells, for example, *Escherichia coli* or *Agrobacterium* cells, preferably the plant cells, and most preferably rice cells. The cells may be isolated, in vitro, cultured, or part of a plant.

The present disclosure provides a brittle culm rice cultivar obtained by using an ibc mutant and through a mutation site of ibc, and use of a brittle culm rice cultivar obtained by loss-of-function mutation in gene IBC by various means, including physical mutagenesis, chemical mutagenesis, biological mutagenesis and gene editing techniques, in straw treatment, including feed and fertilizer products using brittle straw as a raw material.

Preferably, the host cell is a microbial cell.

Preferably, the microbial cell is selected from an *Escherichia coli* cell and an *Agrobacterium* cell.

A method for embrittling cultivated rice culm is provided, including the following step: using a mutagenic means including physical mutagenesis, chemical mutagenesis and biological mutagenesis, or using a gene editing technique, to obtain a rice plant with loss-of-function of the foregoing controlling gene IBC of an ideal brittle culm mutant ibc in rice, where a resulting rice plant exhibits a brittle culm phenotype.

A method for embrittling cultivated rice culm is provided, including the following step: hybridizing an ideal brittle culm mutant ibc in rice having the foregoing mutation site with other rice cultivars, and segregating posterities to obtain a rice plant with a brittle culm phenotype.

The present disclosure provides a brittle culm rice cultivar obtained by using an ibc mutant and through a mutation site of ibc, and use of a brittle culm rice cultivar obtained by loss-of-function mutation in gene IBC by various means, including the foregoing physical mutagenesis, chemical mutagenesis, biological mutagenesis and gene editing techniques, in straw treatment, including feed and fertilizer products using brittle straw as a raw material.

Use of a brittle culm rice cultivar obtained by the foregoing method or brittle straw as a raw material in a feed or fertilizer is provided.

The present disclosure has the following beneficial effects: The brittle culm rice or brittle straw in the present disclosure n is used as a raw material, which is beneficial to chewing and digestion as a feed, and is easy to degrade in the field as a fertilizer.

A second technical problem to be solved by the present disclosure is to provide a method for identifying a mutation site of a controlling gene IBC for culm mechanical strength at the rice ripening stage.

The present disclosure solves the above technical problem by the following technical means:

A method for identifying the foregoing mutation site of an ideal brittle culm mutant ibc in rice is provided, including the following steps:

step 1, performing PCR amplification by using primers ibc-jd-1 and ibc-jd-2, where a forward primer ibc-jd-1-F of the ibc-jd-1 has a nucleotide sequence shown in SEQ ID NO: 4, and a reverse primer ibc-jd-1-R of the ibc-jd-1 has a nucleotide sequence shown in SEQ ID NO: 5; a forward primer ibc-jd-2-F of the ibc-jd-2 has a nucleotide sequence shown in SEQ ID NO: 6, and a reverse primer ibc-jd-2-R of the ibc-jd-2 has a nucleotide sequence shown in SEQ ID NO: 7; and step 2, subjecting amplified products of the primers ibc-jd-1 and ibc-jd-2 to agarose gel electrophoresis detection, where detection results show that: if only the primer ibc-jd-1 has a target band, the mutation site of ibc is homozygous; if only the primer ibc-jd-2 has a target band, the mutation site of ibc is absent and a wild type is defined; and if both of the primers ibc-jd-1 and ibc-jd-2 have target bands, the mutation site of ibc is heterozygous.

The present disclosure has the following beneficial effects: Specific primers for PCR amplification are designed according to the unique mutation type of ibc, the primers are used for PCR amplification on rice DNA to be identified, and rice materials that are homozygous, heterozygous and free of the mutation site of ibc can be clearly distinguished through the agarose gel electrophoresis detection. The method can be used to track and identify the new brittle culm rice cultivars cultivated by using the mutation site of ibc.

The present disclosure has the following advantages: In the present disclosure, a gene IBC for controlling the rice culm mechanical strength is isolated and identified by map-based cloning; the phenotypic analysis and genetic complementation experiment of materials demonstrate the functions of the gene IBC of the ideal brittle culm phenotype in the regulation of mechanical strength and cell wall components of rice culms, and the gene is successfully used to cultivate a brittle culm rice cultivar *Oryza sativa* subsp. *japonica* cv. Kefujing 7 adapted to large-scale production, truly solving the problem of rice straw treatment from the source of the cultivar.

The gene IBC encodes xylan acetyltransferase and plays an important role in the modification of secondary cell wall hemicellulose polysaccharides. In a mutant with allelic variation in gene IBC and loss of gene editing function, culms exhibit a brittle culm phenotype at the late ripening stage, leaves are not brittle, yield traits are excellent, and other agronomic traits are not obviously changed; in the harvest stage, field-harvested culms are easy to crush, crushing and culm returning are facilitated, and the culms are easy to crush into silage in feed processing and to chew and digest by animals.

The gene IBC provides a theoretical basis and material and gene support for elucidating the genetic basis for the regulation of rice secondary cell wall synthesis at the molecular level in the future, and the breeding of environmentally friendly new rice cultivars based on molecular design.

Specific primers for PCR amplification are designed according to the unique mutation type of ibc, the primers are used for PCR amplification on rice DNA to be identified, and rice materials that are homozygous, heterozygous and free of the mutation site of ibc can be clearly distinguished through the agarose gel electrophoresis detection. The method can be used to track and identify the new brittle culm rice cultivars cultivated by using the mutation site of ibc.

DETAILED DESCRIPTION OF THE EMBODIMENTS

Figure 1:
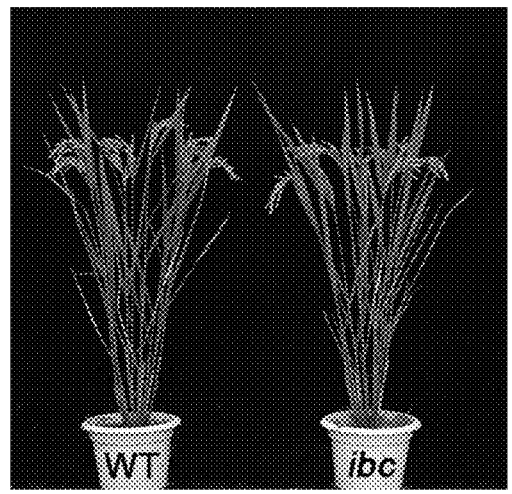
FIG. 1 illustrates a comparison of plant types of a wild type WT versus an ibc mutant in Example 1 of the present disclosure.
Figure 2:
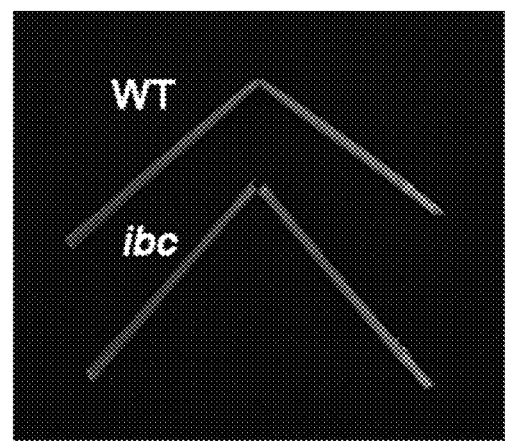
FIG. 2 illustrates a comparison of broken culms of a wild type WT versus an ibc mutant in Example 1 of the present disclosure.
Figure 3:
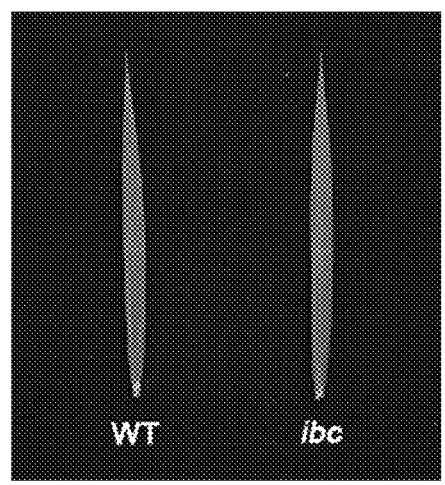
FIG. 3 illustrates a comparison of broken leaves of a wild type WT versus an ibc mutant in Example 1 of the present disclosure.
Figure 4:
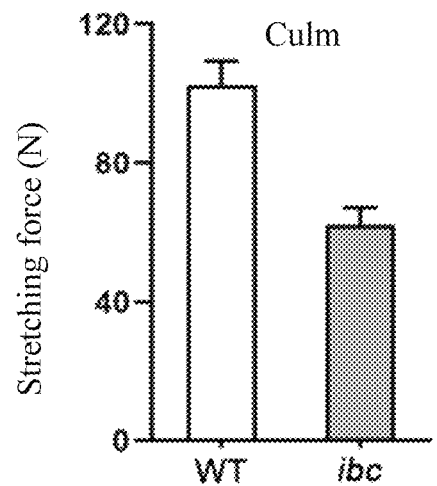
FIG. 4 illustrates a determination result of the culm breaking-resistant strength of a wild type WT versus an ibc mutant in Example 1 of the present disclosure.
Figure 5:
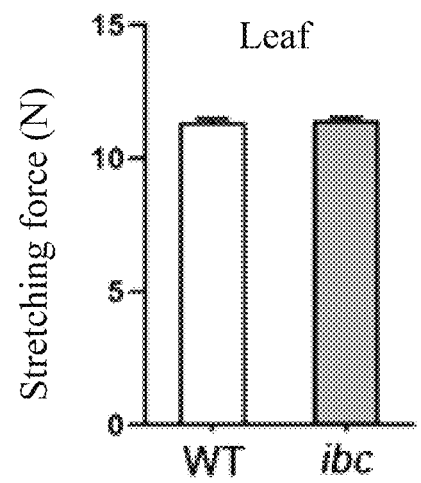
FIG. 5 illustrates a determination result of the leaf breaking-resistant strength of a wild type WT versus an ibc mutant in Example 1 of the present disclosure.
Figure 6:
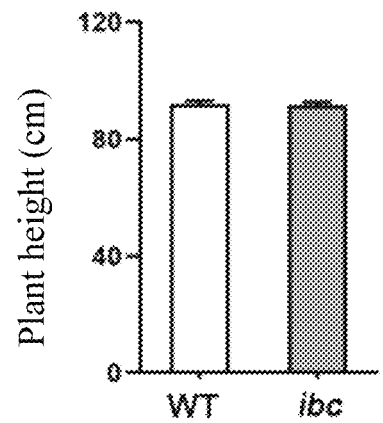
FIG. 6 illustrates a plant height measurement result of a wild type WT versus an ibc mutant in Example 1 of the present disclosure.
Figure 7:
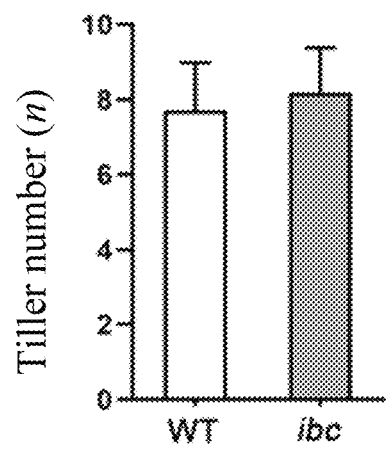
FIG. 7 illustrates a tiller number measurement result of a wild type WT versus an ibc mutant in Example 1 of the present disclosure.
Figure 8:
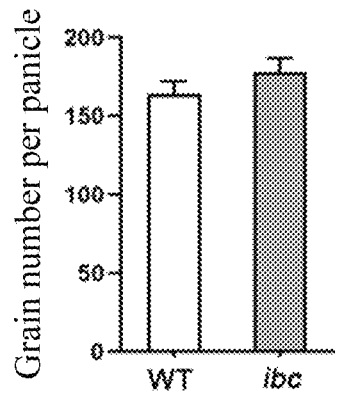
FIG. 8 illustrates a grain number per spike measurement result of a wild type WT versus an ibc mutant in Example 1 of the present disclosure.
Figure 9:
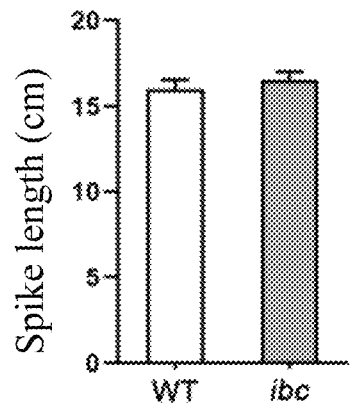
FIG. 9 illustrates a panicle length measurement result of a wild type WT versus an ibc mutant in Example 1 of the present disclosure.
Figure 10:
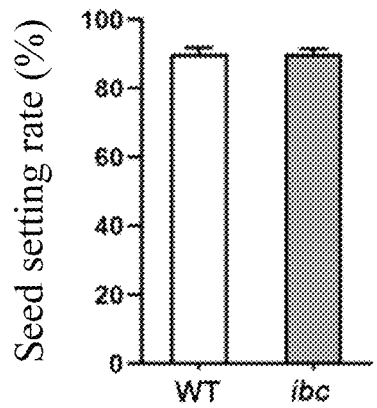
FIG. 10 illustrates a determination result of the seed setting rate of a wild type WT versus an ibc mutant in Example 1 of the present disclosure.
Figure 11:
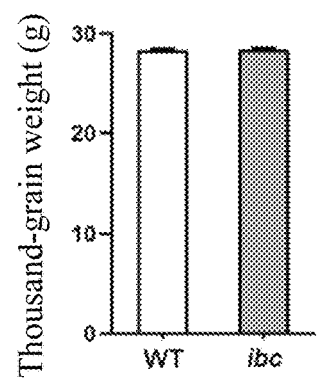
FIG. 11 illustrates a thousand-grain weight measurement result of a wild type WT and versus an ibc mutant in Example 1 of the present disclosure.

In order to make the objectives, technical solutions and advantages of the examples of the present disclosure clearer, the technical solutions in the examples of the present disclosure will be clearly and completely described below with reference to the examples of the present disclosure. Obviously, the described examples are part of, not all of, the examples of the present disclosure. All other examples obtained by a person of ordinary skill in the art based on the examples of the present disclosure without creative efforts shall fall within the protection scope of the present disclosure.

All experimental materials and reagents used in the following examples may be commercially available, unless otherwise specified.

If specific techniques or conditions are not specified in the examples, the procedures shall be carried out in accordance with the techniques or conditions described in the literature in the art or in accordance with the product specification.

Example 1

Phenotypic Analysis of the Ideal Brittle Culm Mutant ibc
(1) Analysis of Agronomic Traits The ibc mutant was obtained by heavy ion $^{12}C^{6+}$ mutagenesis (energy 80 MeV; dose 120 Gy) of *japonica* rice cultivar *Oryza sativa* subsp. *japonica* cv. Wuyunjing 7 (WYJ7). The phenotypic characteristics of the mutant were as follows: at the early heading stage, the plant height, tiller number and growth period were not significantly different from those of the wild type; at the late filling stage, the culm exhibited a brittle culm phenotype, and there were no significant differences in leaf and other agronomic traits, such as grain number per spike, panicle length, seed setting rate, and thousand-grain weight, as shown in FIGS. 1 to 11.
(2) Genetic Analysis of the ibc Mutant In order to investigate the molecular mechanism of ibc mutant forming a brittle culm at the late filling stage, the ibc mutant was first subjected to genetic analysis. Backcross populations were constructed by hybridization of the ibc mutant with wild-type *Oryza sativa* subsp. *japonica* cv. Wuyunjing 7. Among 480 plants in the $F_2$ segregating population, there were 112 plants with brittle culm phenotype and 368 plants with normal culms, and the segregation ratio of brittle culm plants to normal culm plants conformed to 1:3 ($\chi^2$ [1:3]=0.18<$\chi^2$ 0.05=3.84; P>0 05). The ibc mutant was hybridized with *indica* rice cultivar *Oryza sativa* subsp. *indica* cv. Huajingxian 74. Among 600 plants in the $F_2$ segregating population, there were 159 plants with brittle culm phenotype and 441 plants with normal culms, and the segregation ratio of brittle culm plants to normal culm plants conformed to 1:3 ($\chi^2$ [1:3]=0.24<$\chi^2$ 0.05=3.84; P>0.05). The above results indicated that the brittle culm trait of the ibc mutant was recessively controlled by a single gene pair and was not affected by the genetic background.

(3) Scanning Electron Microscopy (SEM) of Cross Sections of Culms

Figure 12:
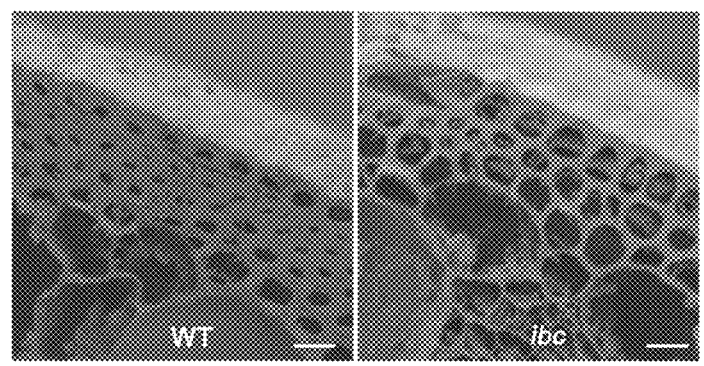
FIG. 12 shows scanning electron micrographs of cross sections of top second culms of a wild type WT versus an ibc mutant in Example 1 of the present disclosure.

In order to further investigate the mechanism of the ibc mutant forming a brittle culm, the cross sections of the top second internodes of the wild type and the ibc mutant were observed by SEM. It was found that the cell wall of the sclerenchyma of the ibc mutant was significantly thinner than that of the wild type (FIG. 12), indicating that the thinning of the secondary cell wall of the sclerenchyma is the cause of the brittle phenotype of the ibc mutant.

Example 2

Figure 13:
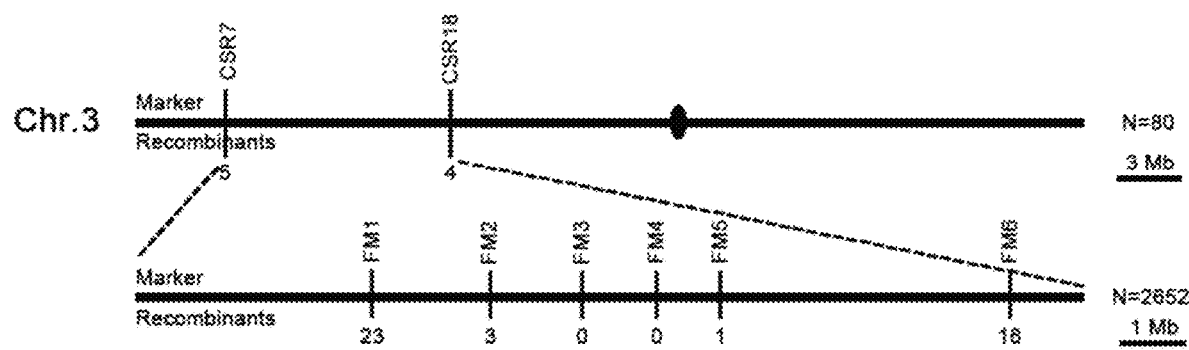
FIG. 13 is a map of a gene IBC in Example 2 of the present disclosure.

Gene Mapping of Ideal Brittle Culm Gene IBC
(1) Construction of Mapping Population The ibc mutant was hybridized with *Oryza sativa* subsp. *indica* cv. 93-11, *Oryza sativa* subsp. *indica* cv. Huajingxian 74, and *Oryza sativa* subsp. *indica* cv. Nanjing 11. The seeds of the segregating population were obtained by selfing the $F_1$ hybrids of different hybrid combinations obtained separately. These seeds were planted in the field. At the late filling stage, individual plants with brittle culm were selected as mapping individual plants. About 100 mg of leaves from each individual plant were used to extract DNA.
(2) Screening of Simple Repeat Sequence (SSR) Polymorphism The polymorphisms of the ibc mutant and *Oryza sativa* subsp. *indica* cv. Huajingxian 74 were screened to obtain polymorphic SSR primers for further experiment by using the reported SSR primers distributed uniformly on rice 12 chromosomes.
(3) Gene IBC Mapping Firstly, 21 random plants were selected from individual plants with brittle culm phenotype in the segregating population constructed by ibc mutant and *Oryza sativa* subsp. *indica* cv. Huajingxian 74 for preliminary mapping of gene IBC. The selected polymorphic SSR primers were used for linkage analysis of these 21 individual plants. The results showed that the molecular markers CSR7 and CSR18 on the long arm of chromosome 3 were significantly linked to the mutant gene. As shown in FIG. 13, the recombinants represent recons. The gene IBC was further determined to be located between CSR7 and CSR18, with an interval of about 8.66 Mb.

In order to further narrow the mapping interval of the gene IBC, more polymorphic primers were searched between CSR7 and CSR18 molecular markers (the primer sequences used for gene IBC mapping are shown in Table 1), and the number of mapping populations was expanded. Linkage analysis was performed on the larger mapping population. As shown in FIG. 13, the recombinants represent recons. Finally, the gene IBC was finely mapped between the Indel markers FM2 and FM5, approximately 3.40 Mb, and co-segregated from the molecular markers FM3 and FM4.

TABLE 1

Primers for gene IBC mapping

| Molecular marker | Sequence of forward primer | Sequence of reverse primer | Physical position (bp) |
|---|---|---|---|
| CSR7 | AAAGTGTTGGTGAGCATAGC, as shown in SEQ ID NO: 8 | TTTGTGTTTGGAGAGACGAG, as shown in SEQ ID NO: 9 | 3804124 |
| CSR18 | ATGTTCAACCTTGTCCCGACT, as shown in SEQ ID NO: 10 | TAAAGACGGCAGCTATCACT, as shown in SEQ ID NO: 11 | 12460908 |
| FM1 | CCCGTGATTTCCTCCGAC, as shown in SEQ ID NO: 12 | TCGCTGGTTCGCTTCATCG, as shown in SEQ ID NO: 13 | 5592412 |

TABLE 1-continued

Primers for gene IBC mapping

| Molecular marker | Sequence of forward primer | Sequence of reverse primer | Physical position (bp) |
|---|---|---|---|
| FM2 | TCAAATGTTCAAAGCCGTACA, as shown in SEQ ID NO: 14 | AAATGGCATATGGGCTCTGT, as shown in SEQ ID NO: 15 | 7105799 |
| FM3 | CCTGGTGGTTAGCAAAAAGC, as shown in SEQ ID NO: 16 | GAAGGCACTGTCAGCTGGAT, as shown in SEQ ID NO: 17 | 8678285 |
| FM4 | AACGTGGGAATTTCTAGCCC, as shown in SEQ ID NO: 18 | GTTTTGGGCCTAAACGAGTG, as shown in SEQ ID NO: 19 | 9889726 |
| FM5 | CATACTCAACACGCAATGCC, as shown in SEQ ID NO: 20 | TATCTGCGACGACGACTCTG, as shown in SEQ ID NO: 21 | 10503841 |
| FM6 | AGTGGCCTACCCGACAAAGT, as shown in SEQ ID NO: 22 | AAAGCTTTTGGGCTCCTCTC, as shown in SEQ ID NO: 23 | 11507516 |

(4) Obtaining of Candidate Genes and Cloning of Gene IBC

Figure 14:
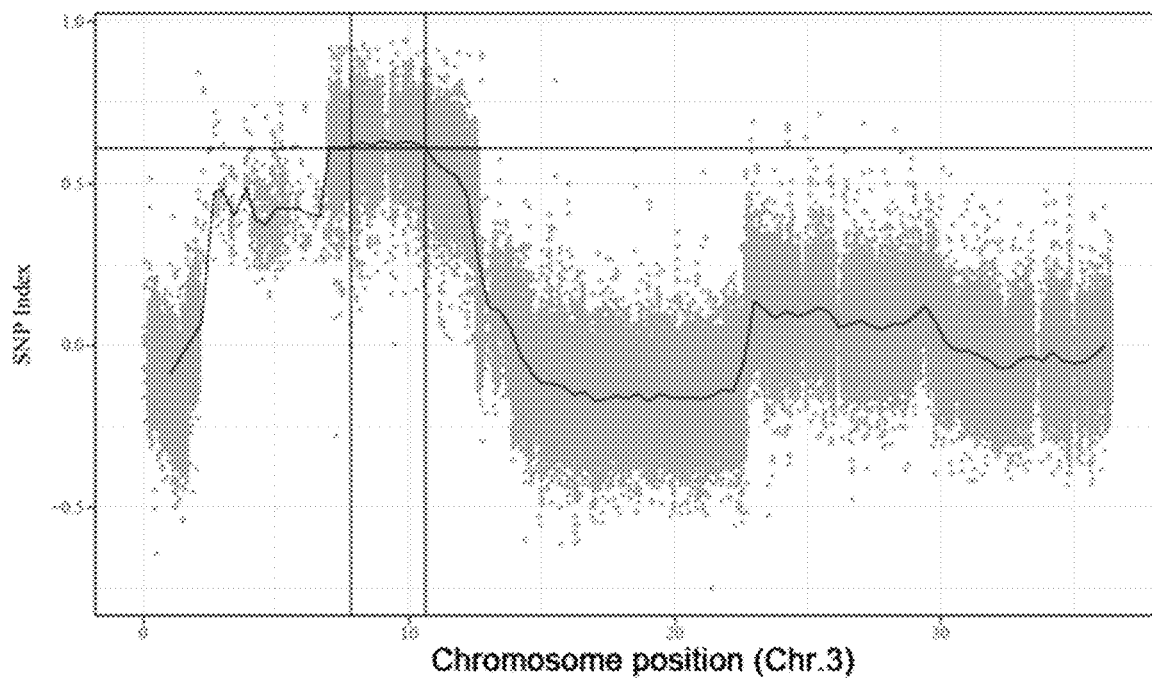
FIG. 14 illustrates a MutMap analysis of a gene IBC in Example 2 of the present disclosure.
Figure 15:
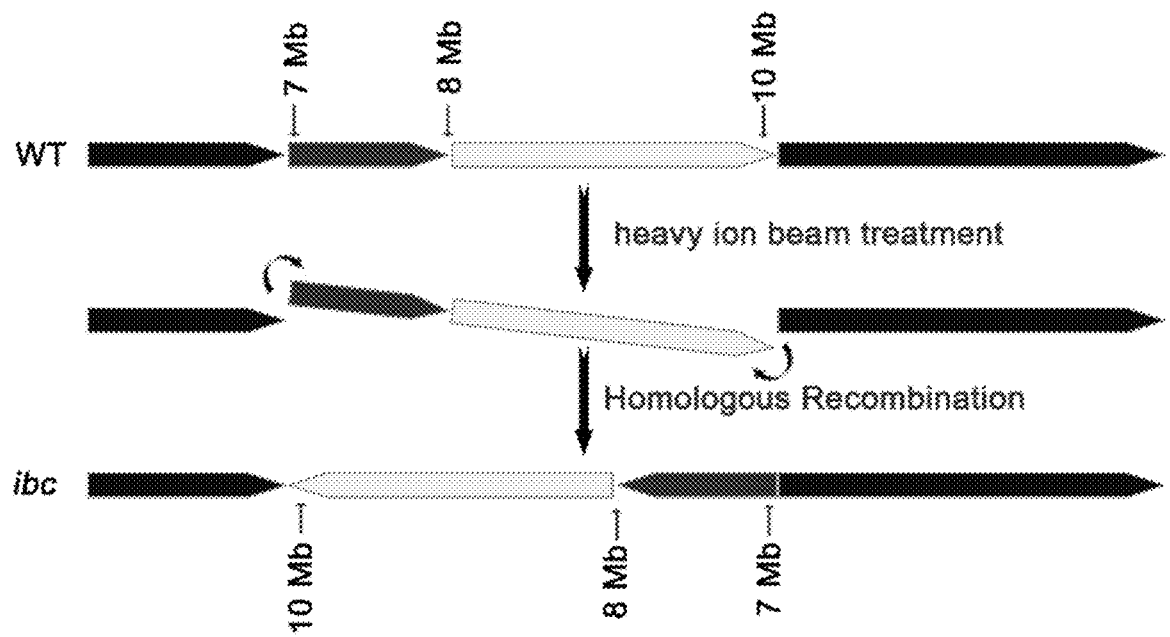
FIG. 15 is a structural schematic diagram of a mutation site of ibc in Example 2 of the present disclosure.

With the development of technologies such as next-generation sequencing (NGS) and third-generation sequencing (TGS) with longer read fragments, there is more selectivity in the mapping of mutant genes of different variation types. Using conventional map-based cloning techniques, the gene IBC cannot continue to narrow the mapping interval, which may be caused by its unique variation type. The gene IBC was considered to be mapped by NGS and TGS. The MutMap mapping results based on NGS were consistent with the above map-based cloning results (FIG. 14). Through the TGS and combined with the NGS results, the genome of the ibc mutant was assembled at a fixed point. The results showed that the ibc mutant had an inversion of a large chromosome segment in the above mapping interval (FIG. 15). The genes at both ends of the inversion were analyzed. It was found that one end of the breakpoint was located on the LOC_Os03g18140 gene, resulting in a loss-of-function mutation in this gene; the position of the other end of the breakpoint did not occur in the coding region of the gene. Therefore, LOC_Os03g18140 was used as a candidate gene for IBC.

(5) Identification of the Mutation Site of ibc

Figure 16:
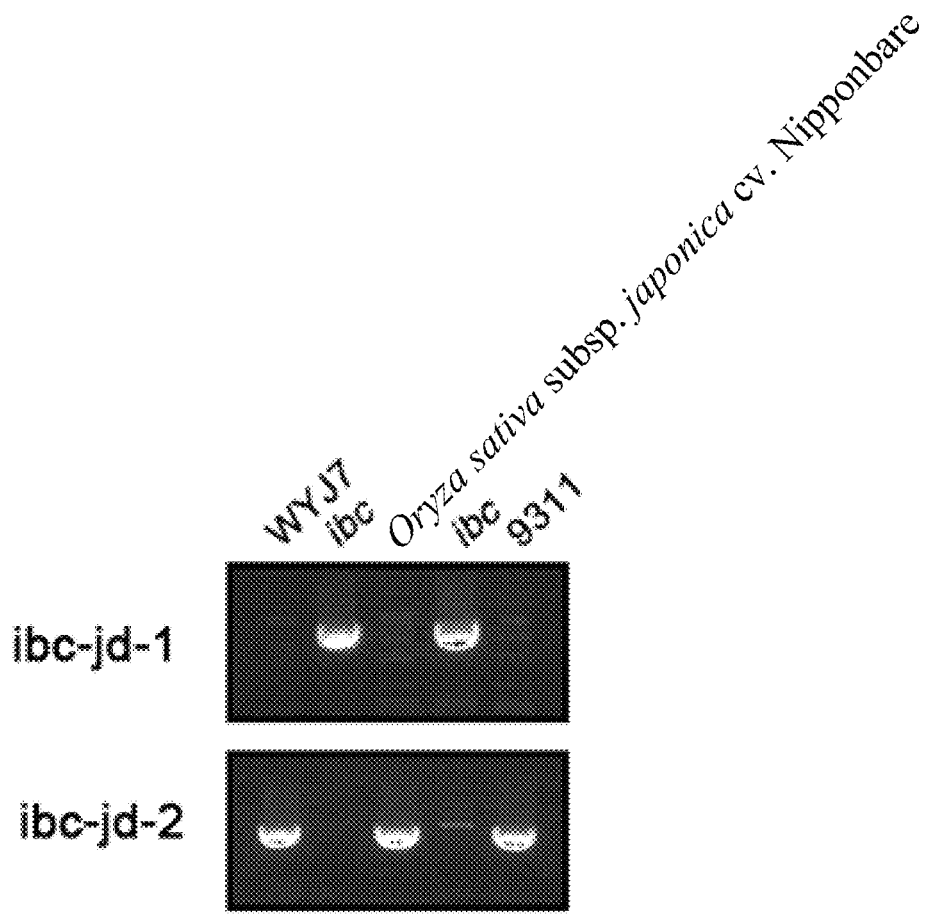
FIG. 16 illustrates an identification result of a mutation site of ibc in Example 2 of the present disclosure.

According to the type of ibc mutation, the corresponding identification primers were designed for PCR amplification. The primer names were ibc-jd-1 (the ibc mutation site could amplify the band, but the wild type could not) and ibc-jd-2 (the wild type could amplify the band, but the ibc mutation site could not), respectively. The identification results showed that the ibc mutant could only use the ibc-jd-1 primer to amplify the band, while the wild type could only use the ibc-jd-2 primer to amplify the band (FIG. 16).

(6) Functional Complementary Verification of Gene IBC

Figure 17:
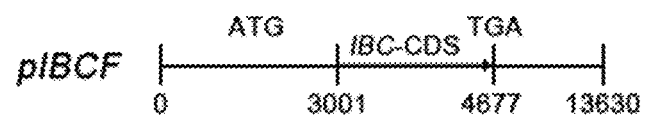
FIG. 17 is a structural diagram of a pIBCF expression vector in Example 2 of the present disclosure.
Figure 18:
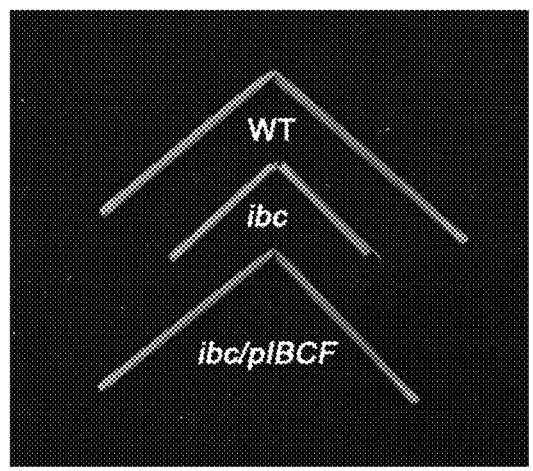
FIG. 18 illustrates a phenotype of a genetic complementary plant in Example 2 of the present disclosure.

In order to verify that LOC_Os03g18140 is the gene IBC, RNA was extracted from the top second internode of the wild type as a material and cDNA was amplified by reverse transcription. An LOC_Os03g18140 expression vector pIBCF driven by LOC_Os03g18140 self-promoter (ATG upstream 3,000 bp fragment) was constructed. The structural diagram of the pIBCF expression vector is shown in FIG. 17. The pIBCF expression vector was transferred into the ibc mutant, and the culms of the positive transgenic $T_0$ plants obtained were all restored to normal levels, as shown in FIG. 18. This result proved that the LOC_Os03g18140 gene was the gene IBC.

The primers used to construct the expression vector pIBCF are as follows:

pIBC-F: 5'-cggaattcTTCACTTTTGGGCATTGTTC-3', as shown in SEQ ID NO: 24 pIBC-R: 5'-cgggtaccCTCCGGAGCGCCCAGGAAGG-3', as shown in SEQ ID NO: 25

IBC-CDS-F: 5'-cgggtaccATGCAGCAGCGGCGGAAGTC-3', as shown in SEQ ID NO: 26

IBC-CDS-R: 5'-cgggatccCTACTGGTCGGATGACCATG-3', as shown in SEQ ID NO: 27

The method for constructing the expression vector pIBCF included the following steps:

(1) The pIBC-F and pIBC-R primers were used to amplify the PCR product with the DNA of wild-type Oryza sativa subsp. japonica cv. Wuyunjing 7 as a template. The PCR product was double digested by restriction endonucleases EcoRI and KpnI, and the pCAMBIA2300 backbone was double digested by the enzymes. Then the amplified pIBC fragment was inserted into the pCAMBIA2300 vector by T4 ligase to obtain an intermediate vector pCAMBIA2300-pIBC.

(2) IBC-CDS-F and IBC-CDS-R primers were used to amplify the PCR product using the cDNA of wild-type Oryza sativa subsp. japonica cv. Wuyunjing 7 as a template. The PCR product was double digested by restriction endonucleases KpnI and BamHI, and the intermediate vector pCAMBIA2300-pIBC obtained in step (1) was double digested by the enzymes. The amplified IBC-CDS fragment was inserted into the pCAMBIA2300-pIBC vector by T4 ligase to obtain a final vector pCAMBIA2300-pIBC::IBC. The vector was pIBCF, as shown in FIG. 17.

Example 3

Method for Cultivating Ideal Brittle Culm Rice Cultivars (1) Cultivation of New Brittle Culm Cultivars by the Mutation Site of ibc The ibc mutant was crossed, backcrossed and selfed with rice cultivars with normal culms, such as Oryza sativa subsp. indica cv. 93-11, Oryza sativa subsp. indica cv. Huajingxian 74, and Oryza sativa subsp. indica cv. Daohuaxiang 2, during which the mutation site of ibc and its genetic background were selected by using identification primers ibc-jd-1 and ibc-jd-2. Finally, a new brittle culm cultivar with homozygous ibc mutant gene under the background of *Oryza sativa* subsp. *indica* cv. 93-11, *Oryza sativa* subsp. *indica* cv. Huajingxian 74, and *Oryza sativa* subsp. *indica* cv. Daohuaxiang 2 was obtained. The specific implementation steps were as follows:

1. $F_1$ hybrids were obtained by crossing recipient parents, such as *Oryza sativa* subsp. *indica* cv. 93-11, *Oryza sativa* subsp. *indica* cv. Huajingxian 74, and *Oryza sativa* subsp. *indica* cv. Daohuaxiang 2, as male parents with the ibc mutant.

2. BC1F1 hybrids were obtained by backcrossing $F_1$ hybrid as a female parent with the recipient parents, such as *Oryza sativa* subsp. *indica* cv. 93-11, *Oryza sativa* subsp. *indica* cv. Huajingxian 74, and *Oryza sativa* subsp. *indica* cv. Daohuaxiang 2.

3. BC1F1 hybrids were planted, ibc genotypes were detected by using identification primers ibc-jd-1 and ibc-jd-2, respectively, the ibc heterozygous genotype was selected, namely, both PCR products of the above the primers ibc-jd-1 and ibc-jd-2 had target bands.

4. The genetic backgrounds of the individual plants selected in step 3 were identified by using molecular markers uniformly distributing on 12 pairs of rice chromosomes (including but not limited to SSR, SNP, InDel, EST, RFLP, AFLP, RAPD, and SCAR markers) and having polymorphisms between ibc mutant and recurrent parent, and the plants with high similarity to the genotype of the recurrent parent (such as more than 75%) were selected.

5. The plants selected in step 4 were backcrossed with the recipient parents, such as *Oryza sativa* subsp. *indica* cv. 93-11, *Oryza sativa* subsp. *indica* cv. Huajingxian 74, and *Oryza sativa* subsp. *indica* cv. Daohuaxiang 2, to obtain BC2F1 hybrids.

6. BC2F1 hybrids were planted, steps 3 and 4 were repeated, plants with heterozygous ibc genotype and high genetic background response rate (such as greater than 95%) were selected, and selfed BC2F2 seeds were harvested.

7. BC2F2 was planted, steps 3 and 4 were repeated, plants with heterozygous ibc genotype and the highest homozygous genetic background were selected, and BC2F3 hybrids were harvested. In ibc homozygous plants segregated from BC2F3 progenies, the detection results of identification primers ibc-jd-1 and ibc-jd-2 showed that only ibc-jd-1 could amplify a target band, and the culm phenotype was a brittle culm phenotype.

(2) Cultivation of New Brittle Culm Cultivars Using Gene Editing Technique

Figure 20:
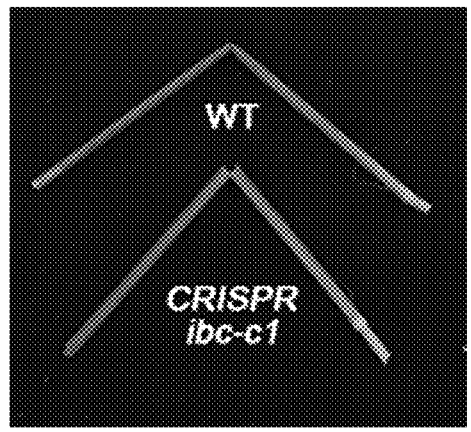
FIG. 20 illustrates a brittle culm phenotype of a CRISPR Cas9-edited plant in Example 3 of the present disclosure.

The gene IBC was edited by using the CRISPR/Cas 9 technology, and a mutant with loss-of-function of gene IBC was created. In several independent homozygous lines with gene IBC knockout, there were no significant differences in other agronomic traits (FIG. 21) except that the culms became brittle at the later stage (FIG. 20).

The construction and transformation method of the CRISPR/Cas 9 vector was as follows:

According to the gDNA sequence of the gene IBC, the target primer was designed as follows:

IBC-CRISPR-U3: 5'-CCTCTACAACGAGGACATCAAGT-3', as shown in SEQ ID NO: 28.

Figure 19:
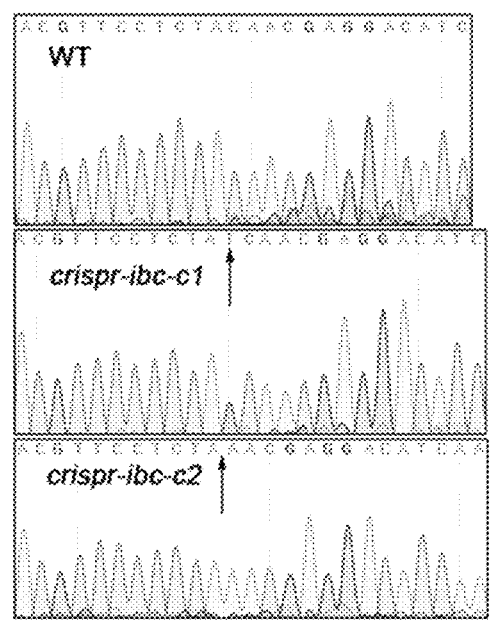
FIG. 19 is a sequencing map of a gene IBC edited by CRISPR/Cas9 in Example 3 of the present disclosure; where the nucleotide sequence the WT is: CCTCTA-CAACGAGGACATCAAGT, as shown in SEQ ID NO: 28; the nucleotide sequence the ibc-c 1 is: CCTCTAT-CAACGAGGACATCAAGT, as shown in SEQ ID NO: 29; the nucleotide sequence the ibc-c 2 is: CCTCTAAACGAGGACATCAAGT, as shown in SEQ ID NO: 30.
Figure 21:
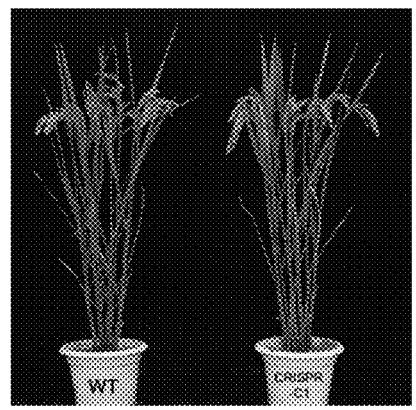
FIG. 21 illustrates a plant type of CRISPR Cas9-edited plants in Example 3 of the present disclosure.

The specific construction method was carried out with reference to the article (A robust CRISPR/Cas9 system for convenient, high-efficiency multiplex genome editing in monocot and dicot plants. (2015) Molecular Plant, 8(8): 1274-1284) published by Prof. Liu Yaoguang in South China Agricultural University. The vector was introduced into WYJ7 by *Agrobacterium*-mediated transformation (rice transformation completed by the applicant's laboratory). Comparing the phenotypic analysis of wild-type and transgenic rice, it was found that in the crispr-ibc (the sequencing peak of the mutation site is shown in FIG. 19) of several IBC-knockout homozygous lines, the culm exhibited a brittle culm phenotype at the later stage (FIG. 20), and there was no significant difference in other agronomic traits (FIG. 21).

Example 4

Figure 22:
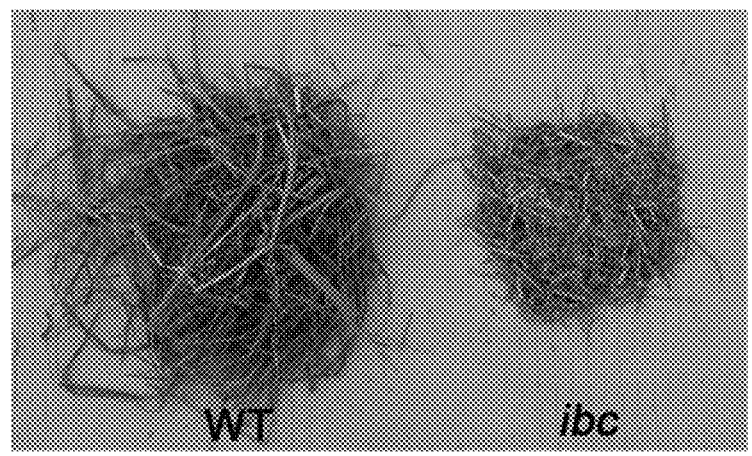
FIG. 22 illustrates chopped straw after wild type WT and ibc mutant materials are harvested in Example 4 of the present disclosure.
Figure 23:
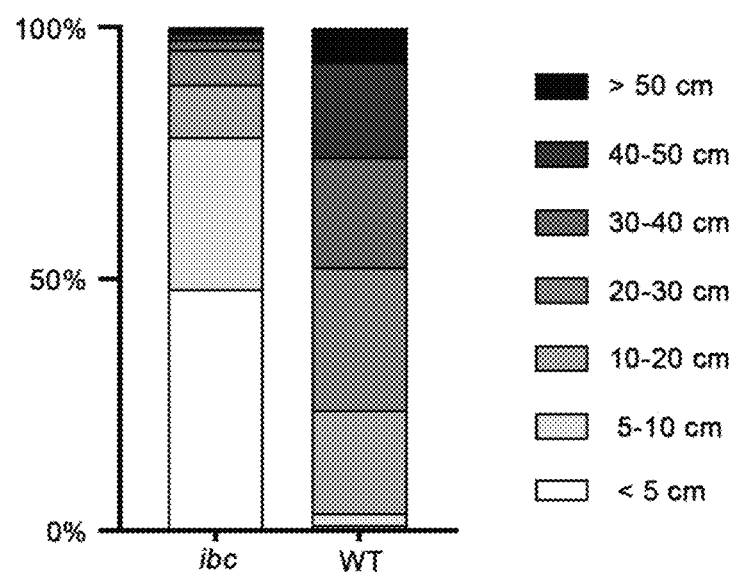
FIG. 23 illustrates a comparison of straw chopping lengths of wild type WT and ibc mutant materials in Example 4 of the present disclosure.

Feed Processing Evaluation of ibc Brittle Culm Rice (1) Straw Field Chopping Experiment The wild type (WT) and ibc mutant materials were planted in a large area, and harvested in the field by a combine harvester during the harvest stage. As shown in FIG. 22, the straw of the ibc mutant was significantly better chopped after harvest than the wild type (WT). According to the statistics of the straw chopping length of a pair of materials, as shown in FIG. 23, the straw length of the ibc mutant after chopping is mostly concentrated in the length range of less than 5 cm and 5-10 cm. This length facilitates the later field degradation of the straw as a raw material for the organic fertilizer, and is also beneficial to the chewing and digestion of the cattle and sheep in the feed.

(2) Goat Farming

In order to evaluate the feeding value of the brittle culm rice, research on the silage of brittle culm rice straw and the feeding of meat goats was carried out. A goat farm with more than 10 years of farming experience and a scale of more than 1,000 goats was selected for experimentation. Firstly, 5 tons each of brittle straw and ordinary straw were collected and processed according to the silage method of whole-plant corn, which was silaged in the form of large package, and the whole-plant corn silage in the same period was used as a control. Bags were opened for sampling and detection two months after silage.

The results showed that the brittle culm feed after silage appeared yellow-green, the sour flavor was very obvious, the texture was soft and non-sticky, and it had the characteristics of high-quality silage. Component detection showed that the content of soluble sugar and starch in silage brittle culm were higher than that of ordinary straw and whole-plant corn, showing excellent nutritional value. By selecting 36 goats of the same size, they were numbered by earmarking and divided into three feeding treatment groups. Each treatment was divided into three goatfolds, with 4 goats in each goatfold. According to the feeding method for using a certain proportion of roughage and fine grain, the goats were fed for two weeks during the pre-test and for two months during the formal test, and weighed every 20 days.

As shown in Table 2, the results show that the silage brittle culm feed has the best feeding effect, the overall weight gain rate is 48.6%, the average daily gain per goat is 137 g, which is 17.1% and 21.2% higher than that of silage corn and ordinary straw, respectively, showing a good application potential.

TABLE 2

The experimental results after feeding silage of brittle culm rice, ordinary rice and whole-plant corn

| Type | Quantity (n) | Initial weight (kg) | Feeding time (day) | Net weight gain (kg) | Daily gain (g) | Weight gain rate (%) |
|---|---|---|---|---|---|---|
| Brittle culm rice | 12 | 186.6 | 60 | 277.2 | 137 | 48.6 |
| Ordinary rice | 12 | 199.0 | 60 | 280.6 | 113 | 41.0 |
| Whole-plant corn | 12 | 193.1 | 60 | 278.0 | 117 | 43.9 |

(3) Cattle Breeding

Forty Holstein cattle: The test cattle were required to have normal growth and development with medium fat, be healthy and disease-free, and grow fast, aged around 4 months, weighing 140-185 kg. The cattle were randomized into four groups of 10 cattle: an ordinary rice straw group (group A), a brittle culm rice straw group (group B), a silage brittle culm rice straw group (group C), and a silage whole-plant corn stalk group (group D). They were fed in groups, twice a day (in the morning and evening). The concentrate limit was 40 kg/day/group, but ordinary rice straw and other test materials were not limited. The feeding time was 8 weeks.

Weight gain effect: The total weight gain was 737.5, 790.5, 825.5 and 841 kg for the ordinary rice straw group (group A), the brittle culm rice straw group (group B), the silage brittle culm rice straw group (group C), and the silage whole-plant corn stalk group (group D), respectively. It was indicated that the effect of the silage brittle culm rice straw was close to that of the silage whole-plant corn stalk, with the potential for alternative use.

Feed palatability: The highest feed intake was 1460.6 kg of silage brittle culm rice straw (group C), followed by 1429.4 kg of the silage whole-plant corn stalk (group D), and the worst was the ordinary rice straw (group A). The intake speed was as follows: silage brittle culm rice straw>silage whole-plant corn stalk>brittle culm rice straw>ordinary rice straw.

The foregoing examples are only intended to explain the technical solutions of the disclosure, and are not intended to limit the same. Although the present disclosure has been described in detail with reference to the foregoing embodiments, it should be understood by those of ordinary skill in the art that the present disclosure may still be modified with reference to the foregoing embodiments, or equivalent substitutions may be made to some of the technical features in the foregoing embodiments, and these modifications or substitutions do not make the nature of the corresponding technical solutions depart from the spirit and scope of the technical solutions of the embodiments of the present disclosure.

What is claimed is:

1. A method for identifying a mutation site of an ideal brittle culm mutant ibc in a rice, comprising the following steps:

step (1), performing a polymerase chain reaction (PCR) amplification by using primers ibc-jd-1 and ibc-jd-2, wherein a forward primer ibc-jd-1-F of the ibc-jd-1 has the nucleotide sequence shown in SEQ ID NO: 4, and a reverse primer ibc-jd-1-R of the ibc-jd-1 has the nucleotide sequence shown in SEQ ID NO: 5; a forward primer ibc-jd-2-F of the ibc-jd-2 has the nucleotide sequence shown in SEQ ID NO: 6, and a reverse primer ibc-jd-2-R of the ibc-jd-2 has the nucleotide sequence shown in SEQ ID NO: 7;

step (2), subjecting amplified products of the primers ibc-jd-1 and ibc-jd-2 to an agarose gel electrophoresis detection, wherein detection results show that: if only primer ibc-jd-1 has a target band, the mutation site of the ideal brittle culm mutant ibc is homozygous; if only primer ibc-jd-2 has a target band, the mutation site of the ideal brittle culm mutant ibc is absent and a wild type is defined; and if both of the primers ibc-jd-1 and ibc-jd-2 have target bands, the mutation site of the ideal brittle culm mutant ibc is heterozygous;

wherein the mutation site is a chromosomal segment inversion, and the chromosomal segment inversion is located on an LOC_Os03g18140 gene.

* * * * *

SEQUENCE LISTING

```
<160> NUMBER OF SEQ ID NOS: 30

<210> SEQ ID NO 1
<211> LENGTH: 8541
<212> TYPE: DNA
<213> ORGANISM: Rice

<400> SEQUENCE: 1
gttgaagcat agatatctga taggccagta cttgctccac tcgtgtggtt aaacaaagag      60
gggcacatta ttaggagtaa tagacaaaaa tcgccatagt ttctagccta cgattcaaaa     120
agagaaccac ccaattcact tttgggcatt gttcatcgac ttgacttgga ctgccctgtt     180
atcagaatta ggttcgctgg gatgacatga tttaaaagca tcaatgattt gcacctaaaa     240
tgtgaatgac atattgacat tcctactact gtagagagaa acatcattct gacaaaagaa     300
acactacaga aaaacgaaat ttcctccagc agttgcagag aggaactttt catctctccc     360
gtggtcttgg atcctctatt tcccacgttg gctgaaatgc aagcttattc tgaactgtcc     420
gtctggatga tgggcgagat tcaggtaaaa aagaagcatg gtgttcaggt tgcatgcgat     480
tcaatcatct atgtcatgtt catgtggaaa aaatttattg agctggccca agtgcctgct     540
ccagtgttcc tggactcaat tataaccaaa tcatactagc tagagtagtt gacttcagcg     600
atgccggctg cgctacactc atcgaccagc agtgttgaga acccatcata gctagctcaa     660
tgtgacttta ggttattgaa gttttcttta ttatcttaac acgagatgga ggtcagagtg     720
tcagaccggg atctccatga tggagtataa aacattgatg ttattaaact acgtagcata     780
tgcctatttg gactgaagat tggatcagga tagtggttca gctgtacttc cctcagaatc     840
agtaagtata ccgtatagca ctcaacaaag cgaggcaaca ggtttggagt attcgaacaa     900
gacataagtt tggagtaatt tgtaccggtg gttgcaatca gagggggaaa tggtgtgtgc     960
aaccgttttc tctataatag catgttggga aacactttta atcgcctagg tggacatcca    1020
```

```
cctatttgtt gcatgtcaac taaataggta tgaaaaaaaa tcaaaaaaat tccagaaaaa      1080
tagtagtaac tgtatgctag taagaggatt ggttcccata ggtgtaacca aacagcaaag      1140
ataccaccag actgatcggt gcttgtgagc gagctcaaga agaactggac atctgaacat      1200
tcaactgatt gcttccagct atggaataac ctgaagaagg aaaatggact gtgttataca      1260
tacattgctg ttctctctct ttttttttaa cagggaattg aatttctctg tctctcagaa      1320
aattatctgt taaacctgta gttgttctcg aaaataaaaa ctgtagacct caatgtaaca      1380
agatgttacc catggaagat ggatgagagc atttctcccg atgaacaaca aaataataga      1440
gtggaaagtt cctgatcacg acttcacgag ttacagcaaa ctaaacaaga gctgggtcca      1500
agatgtttca gtttcttccg atttctcgga tccatgtctc cactctccac acattgttaa      1560
tgttctcaac ttaacagaag aatcattttt acagcaagtg atcaatgaaa aataatagta      1620
tctgacaatg atattctttt gaaaaagaa atattcgac cctacatagg cacatcattt      1680
gagatctgga agttgaaaga aaatgataac agacagtgat atcaattcgt atgcgtacta      1740
gctaagacga gttggcgtga caagattgga aacatattga acaccgcag aaaagcactg      1800 tgtaaaaact gaaacgtgtt atactctaca gaaacaggac aaccgactct gaaagatgca      1860
ccgattctct gattttttg caaggctatt ctgtgacctg aaatttcagt cacctatgct      1920
gtacacggtg ctttcatttt cccctgtaa tatccatttt ctgctcgaaa cattggtcct      1980
attaaatcaa cctctgacca tgactaacat cacttcctga caatgatttt cgtagacca      2040 atcccccga acactgtcga tcggaacaat tcgacattct gcagtttcct cctgctgcaa      2100
cactatctga aaatcggaac gattcaggca ccgtatcgtt gtctgattcg tcgattcgtt      2160
ccatcattag tgtgttcaca acgcaaagac gatgactgta gtagtatctg cgtgctgatt      2220
acatccaaat acagaatgat catctccgag aatgcgaaag gggggcaatt gacgtagccg      2280 ccccgccgt tgtttgcttc cccatctcgc actcttccga gacagccacg gcctacccac      2340
tcacatcgca taaacaaaaa acgagtactt acaaccatac gagtatacac cataatacca      2400
tatactccac ccctgtatcc cgataatgaa acgaaatgt atgatatagt aggcatataa      2460
ttaaaacatg caacgaacaa atagaatact agtagtagaa tacacacacg cacattgcct      2520
gtgttgttac atgtgtacaa cagcttaacc tccaaacccc ccatggaagc tttgcagcct      2580
tgcatgttac tcatttgacc caccccctcag tagtagtact accctctatc tctctatata      2640
caaaatgaaa gggaatgaga ttcaattaag cagctagaac aggggggagt ttacaagtgt      2700
tggtggaggg gaagagatct tgcaaccata aagaagaaa gcaggcgaac caaaccaaac      2760
ataccaaagg gaagcaaaga aaagggcaaa catccagcaa aagtcaccaa acttgtaaag      2820
ggatcgacac atatatagga gagcgaggtg tccagtcgag aaggacagcc aggccaagga      2880
gctcctagcc tcctagccta cacagagcta agcaaagagg caaagagctc agcaagaagc      2940
tccattaatc cattccatat actcatatag agaggaggag gaggaggaag aggaagagag      3000
gggaagcaaa gcaagaagct tttttactt ctcgggtttg caagccaccg ggaaaggccg      3060
gggcttggtg gtggtggtgg tggtaagttt tctttaaagc ggcggagcgg gaggccttcc      3120
tgggcgctcc ggagatgcag cagcggcgga agtcggtgtt cgcctcggcg ccgttcgcga      3180
tgaagcaggc ggcgctgggg gccggcgtgg cggcgcgcag gaacggcgcg ccgctgtcgc      3240
tggcggcggt ggtgttcgcg ctcttcgtgt tcgcgacgtt cctctacaac gaggacatca      3300
agtccatcgc cgacttcccc ttcggcgccg gcgcgctccg cgccaagtcc cccgacctcc      3360
```

```
acgtcctcca ggagaccgtg ggcgccgcgc acctcgccgc cggcagcatc gccaagcgcg     3420
gcgaggaggt catcgtccgt gtcctcgacg cgcccgcctc cacggcgatg gcggccgccg     3480
ccggcagcag cagcaacaac agcacgattg aggtggccaa ggccaatgcc aacgccaacg     3540
ccaacgccgc cgacgccggt gtcaaggtgg acgaggggca ggagagggag cgggacgtga     3600
cgctcccgag tgtcaaggaa ggcggcgccg acgaggcgag gcggcgggag gacgaggagg     3660
ccgccgagaa ggagtcctcg gcgaaggccg ccgcggcgac ggcggcgctg cggaccgtgg     3720
tgagcgtgcc ggacacctgc gacctgtacc gcggcaactg ggtgtacgac gaggtgaacg     3780
cgccggtgta caaggagtcg cagtgcgagt cctgacggga gcaggtcacc tgcatgcgca     3840
acggccgccg cgacgactcc taccagaagt ggcgctggca gccgaccgac tgcgacctgc     3900
cccggtacgc catttcttcc cccacaattt tttcacgcca tttcttgccc aatttcgtgc     3960
cgtttcacgc aattccgggt aaccggcatt gactcacgcc ggcgatcatc gtcggtttcc     4020
caaattgatg ccggtttcta ccctttctt tttctttttt catcagcatc ggtcggtcac     4080
ctcgaaacgc taagtcagaa ataaccgtag gaatacttac gggccaaaat taagacgaac     4140
gtgtcaggga aattaaaata gaacgttcga gattttgaa acggaacaga gagtagtagt     4200
accaccatgc cacaccagta caccactctg gtagtgagct gtgacgtcgg actgtactgt     4260
gcagccgcgc taccccctgt tggattaagc tttgcttaat ctaatcactc agcatctggc     4320
tgctgttgaa gcaccacta cttaaatcaa acacaggcac gccaaattat tctcttttcc     4380
aaccggggaa cagctgcacg cagcgacgcc cagtcagtca cacagtgggt gagtgacgcg     4440
agtagaatat actactacaa cttgctctgt atctgtgtct cggcacagtc tgatgatagt     4500
ggcaaatata gttggcgatc caacaacgct ggttgctaaa taacgcagga aaagtctaac     4560
gaaagctgat gtggtgtggg gaaaaaaaaa ctgcaggttc gacgcgaggc tgctgctgga     4620
gcggctgcgc aacaagcggc tgatgttcgt gggggattcg ctgaaccgca accagtggga     4680
gtcgatggtg tgcctggtcc agtccgtgat ccccaagggc aagaagacgc tcaccaagtt     4740
cgtcaacggc ggcaacagca acatcttcta cgcacacgta cgtagcaggc atcagcaacg     4800
tcacgtacgt actccgctgt cgatccgaca tgatctcccc ctgacgatac ggtgtatgtg     4860
ctacgtgcag gagtacaacg cgacggtgga gttctactgg gcgccgttcc tggtggagtc     4920
gaactcggac aacccgcagg tgcacagcgt ccccgaccgc gtcatccagt ggcactccat     4980
cgccaagcac gcgcacaact ggctcggcgt cgactacctc atcttcaaca cctacatctg     5040
gtggctcaac accctcgaca tgaaagtcct gtaagttgta ctcctagcac cccagcagcg     5100
tacacacata catatagtga tatagaagtg ggtgtgctga tctgggcgaa aaaatatgtg     5160
tgtggttgta cgtgacagga agggtcgtt cgaccaggt gcgacggagt acgtggaggt     5220
ggaccggccc gtggcgtaca aggaggtgct caagacgtgg gcgaagtggg tcgaccgcaa     5280
cattgacccc aaccggacga ccgtcttctt catgagcatg tctcccaacc acatcacgta     5340
agccgccatt tatgcctttg cctgcatctg cattgcattg cccctctcca tgatttactt     5400
cgctgcacag tgcacacgtg cccacgcgca gtacagttcg ctcggagtta atctaccaat     5460
caataggaag atatgctgca cagtgatggt acatagagaa ctccattccg attaggtgtt     5520
ggggtatgtt cagaaaacaa aattaggtgc ttgaggtgta cctagcaact gtgttgcgtt     5580
tgcaaggagg aaacttagct agcagccaca cttgctttct ggactaatag taatctacaa     5640
gtaatttaat taggtggtga gagcctgagg ggactcgtga gctttcggag aaacattagt     5700
agtagaagcc tcttatacat taactagcta ctagtagcat ggtatcggaa tacaactgca     5760
```

```
catggtatcc catcatagag cactgtacta ctcatcggta gctgtctctc gtgaaatggc    5820
atcgtggggc acggtacctg cgtacaacgc gtcactgtac ttcgtcagga catggtccgg    5880
acaatctgtt ctgactggtt caagatttgc attttttcacg gtttcaacac tggtatctaa    5940
gcttctttag ccaatactat aaaaagctta attaattagt gagatgtctt caaaacatgc    6000
tagttgacgt gggtgtagaa caactgagg tttgttgaac caagaataat tcaaattgag    6060
tatgtatttg tgtagagtag taagctcaaa actagtcatg tggatagctg gagagaggcg    6120
agctacggtg acaagctgat gttggtggac catagaaaat cccaggccca cctgtaggca    6180
tgcatctcga catggcccac cctagtcgct accaaagatg aagcatacga atccaattcc    6240
ccgagctcca tgtcactttc cttcctcgag ccctaacccc acgaaagaga aacgacatca    6300
agttgaaggt agcaacaaaa gacagtagta taatactgat agcaatcaag cctactaatc    6360
gtgctccaca atgatgatca gcctttgcca ttgcatcttt gctgttgcaa atactcaaa    6420 acagagagat tcttgcagta gtcgacaagc aaaagttaaa tcagttttgg tccctgcaag    6480
aatctcgagc tagtatccgc ataaattaca cggtccgtgc atatgctgtg ataatggcgc    6540
caatatgcga gtgccatcat catcagggta tcatcagcac gacagaatct agggtaccac    6600
ggctccaatt cgctggaaca ttaaccatag tactgcatca gaattctacc catcacggca    6660
tcacgtggtg acgacggat ggtggtataa tcttgtgtcg tgtgcgcgtt ttgtggcagg    6720
ccggaggcgt ggggaaacta cggagggatc aagtgcgcga tggagacgct gccgatcacg    6780
aaccggacga cgtcgctgga cgtgggcacg gactggaggc tgtacgccgg ggcgcaggag    6840
gtgctccaga cgttccgccg ggtgccggtg cacctcgtcg acatcacggc gctgtcggag    6900
ctccgcaagg atgcgcacac gtcggtgcac acgctccggc aggggaagct gctcacccc    6960 gagcagcagt ccgaccccaa gacgtacgcc gactgcatcc actggtgcct cccgggcctc    7020
cccgacacct ggaaccagtt cctctacgcc cgcatcgcct ccgccccatg gtcatccgac    7080
cagtagaaaa agagccaaat aaggctagct tccaagtgtt ctgcgagaca agaaaggag    7140 ccaagaacac cgttgacaca ccatcgatgc ccgccgcccg gccgcggcca cctcactttt    7200
tcttactttg ggttactttt ttttcttctc tttttttcac catttttctt tctttctctg    7260
gggttgcgta aagctgtctt gtgctgtgtt taacatgtga ttcttttgtt aaaaagaaa    7320 tggagggttt aggatggtga aggaggatct gtgggcgggc tgtgttgact atagctcatt    7380
tcttgtcctg ctgataaagg atgcatggat aggagaaagc aaaaaaaggg tgtgatgtga    7440
gatgtaaggg gggaaagaaa aagggagggt tacatgtaaa gaattttgt gtattacacc    7500 attctagtac attgatgctc aagagaggta taaaggccac gaggtgcatc cgttcttcaa    7560
ttatgatgat gattcctaag tttctccttt tcattttatt acactgagtg atcacttcac    7620
tccacctact gttccggaac tactactatg cacgaatgtt cagaaaagag attggcaatg    7680
gaataacaca gtctgcactt ctctgaagat aattgtaggg gaataaagct ccggaagcgt    7740
gcatagctcc ccttttctctt tactcttatc tttaggcaaa ctgtgagcaa agcaactcag    7800
ctacattcat tcagtctata ctttttctgca cgcagggtca aattacccag caaaatctct    7860
ggttaccaat agcatgagtg catgacaaag gccatagcca aacgggactg cctatagatc    7920
atttgataga aaatccctt agaaatctta caaattttgg accaccgat tgctttaaga    7980 tttatgcatc aaccaaaccc tataaaacct tctcctctca ttcccctca cgccgccact    8040 cctcgttagc gtgagcgtat tccgcgttgc cgccgccacc cggtcccgcc ggcgagcccc    8100
```

| | |
|---|---|
| cccctcccct ctccccctc cagccatcga aggcaagatg ctcccgtccc gtcgtgtctg | 8160 |
| gcaactcctc gccgccggat ccgccaccat cggccaccac aaggcacaag cttgctatgc | 8220 |
| ccccgccacc aacactggcc caccgccctc ctccatccca gcagctctgg tgtcgccgcc | 8280 |
| tcgccgccca cccgtcctgc tacccaccgc taggccgctg cctcccacga ccatccatct | 8340 |
| aagcccggtg aactccccct tcttcccct cccctcccc ctccatccc acctcacccc | 8400 |
| accccaagag cctaattcat tggccctccg ccagagtttg ggttgtcact gacaggggca | 8460 |
| taggagttgg agaagaagca gctggagcac gaattgcgaa gcacataaaa tctgcaagat | 8520 |
| ttagagatag atttttctgt c | 8541 |

<210> SEQ ID NO 2
<211> LENGTH: 1677
<212> TYPE: DNA
<213> ORGANISM: Rice

<400> SEQUENCE: 2

| | |
|---|---|
| atgcagcagc ggcggaagtc ggtgttcgcc tcggcgccgt tcgcgatgaa gcaggcggcg | 60 |
| ctggggccg gcgtggcggc gcgcaggaac ggcgcgccgc tgtcgctggc ggcggtggtg | 120 |
| ttcgcgctct tcgtgttcgc gacgttcctc tacaacgagg acatcaagtc catcgccgac | 180 |
| ttccccttcg gcgccggcgc gctccgcgcc aagtcccccg acctccacgt cctccaggag | 240 |
| accgtgggcg ccgcgcacct cgccgccggc agcatcgcca gcgcggcga ggaggtcatc | 300 |
| gtccgtgtcc tcgacgcgcc cgcctccacg gcgatggcgg ccgccgccgg cagcagcagc | 360 |
| aacaacagca cgattgaggt ggccaaggcc aatgccaacg ccaacgccaa cgccgccgac | 420 |
| gccggtgtca aggtggacga ggggcaggag agggagcggg acgtgacgct cccgagtgtc | 480 |
| aaggaaggcg cgccgacga ggcgaggcgg cgggaggacg aggaggccgc cgagaaggag | 540 |
| tcctcggcga aggccgccgc ggcgacggcg gcgctgcgga ccgtggtgag cgtgccggac | 600 |
| acctgcgacc tgtaccgcgg caactgggtg tacgacgagg tgaacgcgcc ggtgtacaag | 660 |
| gagtcgcagt gcgagttcct gacggagcag gtcacctgca tgcgcaacgg ccgccgcgac | 720 |
| gactcctacc agaagtggcg ctggcagccg accgactgcg acctgccccg gttcgacgcg | 780 |
| aggctgctgc tggagcggct gcgcaacaag cggctgatgt tcgtggggga ttcgctgaac | 840 |
| cgcaaccagt gggagtcgat ggtgtgcctg gtccagtccg tgatcccaa gggcaagaag | 900 |
| acgctcacca agttcgtcaa cggcggcaac agcaacatct tctacgcaca cgagtacaac | 960 |
| gcgacggtgg agttctactg ggcgccgttc ctggtggagt cgaactcgga caacccgcag | 1020 |
| gtgcacagcg tccccgaccg cgtcatccag tggcactcca tcgccaagca cgcgcacaac | 1080 |
| tggctcggcg tcgactacct catcttcaac acctacatct ggtggctcaa cacctcgac | 1140 |
| atgaaagtcc tgaagggtc gttcgaccag ggtgcgacgg agtacgtgga ggtggaccgg | 1200 |
| cccgtggcgt acaaggaggt gctcaagacg tgggcgaagt gggtcgaccg caacattgac | 1260 |
| cccaaccgga cgaccgtctt cttcatgagc atgtctccca ccacatcac gccggaggcg | 1320 |
| tggggaaact acggagggat caagtgcgcg atggagacgc tgccgatcac gaaccggacg | 1380 |
| acgtcgctgg acgtgggcac ggactggagg ctgtacgccg gggcgcagga ggtgctccag | 1440 |
| acgttccgcc gggtgccggt gcacctcgtc gacatcacgg cgctgtcgga gctccgcaag | 1500 |
| gatgcgcaca cgtcggtgca cacgctccgg caggggaagc tgctcacccc cgagcagcag | 1560 |
| tccgaccca gacgtacgc cgactgcatc cactggtgcc tcccgggcct ccccgacacc | 1620 |
| tggaaccagt tcctctacgc ccgcatcgcc tccgcccat ggtcatccga ccagtag | 1677 |

<210> SEQ ID NO 3
<211> LENGTH: 558
<212> TYPE: PRT
<213> ORGANISM: Rice

<400> SEQUENCE: 3

Met Gln Gln Arg Arg Lys Ser Val Phe Ala Ser Ala Pro Phe Ala Met
1               5                   10                  15

Lys Gln Ala Ala Leu Gly Ala Gly Val Ala Ala Arg Arg Asn Gly Ala
            20                  25                  30

Pro Leu Ser Leu Ala Ala Val Val Phe Ala Leu Phe Val Phe Ala Thr
        35                  40                  45

Phe Leu Tyr Asn Glu Asp Ile Lys Ser Ile Ala Asp Phe Pro Phe Gly
    50                  55                  60

Ala Gly Ala Leu Arg Ala Lys Ser Pro Asp Leu His Val Leu Gln Glu
65                  70                  75                  80

Thr Val Gly Ala Ala His Leu Ala Ala Gly Ser Ile Ala Lys Arg Gly
                85                  90                  95

Glu Glu Val Ile Val Arg Val Leu Asp Ala Pro Ala Ser Thr Ala Met
            100                 105                 110

Ala Ala Ala Ala Gly Ser Ser Ser Asn Asn Ser Thr Ile Glu Val Ala
        115                 120                 125

Lys Ala Asn Ala Asn Ala Asn Ala Asn Ala Asp Ala Gly Val Lys
    130                 135                 140

Val Asp Glu Gly Gln Glu Arg Glu Arg Asp Val Thr Leu Pro Ser Val
145                 150                 155                 160

Lys Glu Gly Gly Ala Asp Glu Ala Arg Arg Glu Asp Glu Ala
                165                 170                 175

Ala Glu Lys Glu Ser Ser Ala Lys Ala Ala Ala Thr Ala Ala Leu
            180                 185                 190

Arg Thr Val Val Ser Val Pro Asp Thr Cys Asp Leu Tyr Arg Gly Asn
        195                 200                 205

Trp Val Tyr Asp Glu Val Asn Ala Pro Val Tyr Lys Glu Ser Gln Cys
    210                 215                 220

Glu Phe Leu Thr Glu Gln Val Thr Cys Met Arg Asn Gly Arg Arg Asp
225                 230                 235                 240

Asp Ser Tyr Gln Lys Trp Arg Trp Gln Pro Thr Asp Cys Asp Leu Pro
                245                 250                 255

Arg Phe Asp Ala Arg Leu Leu Leu Glu Arg Leu Arg Asn Lys Arg Leu
            260                 265                 270

Met Phe Val Gly Asp Ser Leu Asn Arg Asn Gln Trp Glu Ser Met Val
        275                 280                 285

Cys Leu Val Gln Ser Val Ile Pro Lys Gly Lys Lys Thr Leu Thr Lys
    290                 295                 300

Phe Val Asn Gly Gly Asn Ser Asn Ile Phe Tyr Ala His Glu Tyr Asn
305                 310                 315                 320

Ala Thr Val Glu Phe Tyr Trp Ala Pro Phe Leu Val Glu Ser Asn Ser
                325                 330                 335

Asp Asn Pro Gln Val His Ser Val Pro Asp Arg Val Ile Gln Trp His
            340                 345                 350

Ser Ile Ala Lys His Ala His Asn Trp Leu Gly Val Asp Tyr Leu Ile
        355                 360                 365

Phe Asn Thr Tyr Ile Trp Trp Leu Asn Thr Leu Asp Met Lys Val Leu

-continued

```
                    370                 375                 380
Lys Gly Ser Phe Asp Gln Gly Ala Thr Glu Tyr Val Glu Val Asp Arg
385                 390                 395                 400

Pro Val Ala Tyr Lys Glu Val Leu Lys Thr Trp Ala Lys Trp Val Asp
                405                 410                 415

Arg Asn Ile Asp Pro Asn Arg Thr Thr Val Phe Phe Met Ser Met Ser
                420                 425                 430

Pro Asn His Ile Thr Pro Glu Ala Trp Gly Asn Tyr Gly Gly Ile Lys
                435                 440                 445

Cys Ala Met Glu Thr Leu Pro Ile Thr Asn Arg Thr Thr Ser Leu Asp
                450                 455                 460

Val Gly Thr Asp Trp Arg Leu Tyr Ala Gly Ala Gln Glu Val Leu Gln
465                 470                 475                 480

Thr Phe Arg Arg Val Pro Val His Leu Val Asp Ile Thr Ala Leu Ser
                485                 490                 495

Glu Leu Arg Lys Asp Ala His Thr Ser Val His Thr Leu Arg Gln Gly
                500                 505                 510

Lys Leu Leu Thr Pro Glu Gln Gln Ser Asp Pro Lys Thr Tyr Ala Asp
                515                 520                 525

Cys Ile His Trp Cys Leu Pro Gly Leu Pro Asp Thr Trp Asn Gln Phe
                530                 535                 540

Leu Tyr Ala Arg Ile Ala Ser Ala Pro Trp Ser Ser Asp Gln
545                 550                 555

<210> SEQ ID NO 4
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 4
gaggaactgg ttccaggtgt                                              20

<210> SEQ ID NO 5
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 5
gtggcactag cacacacgat                                              20

<210> SEQ ID NO 6
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 6
ccaccctagt cgctaccaaa                                              20

<210> SEQ ID NO 7
<211> LENGTH: 20
<212> TYPE: DNA
<213> ORGANISM: Artificial Sequence
<220> FEATURE:
<223> OTHER INFORMATION: The sequence is synthetized.
```

```
<400> SEQUENCE: 7
gcacttgatc cctccgtagt                                                  20

<210> SEQ ID NO 8
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 8
aaagtgttgg tgagcatagc                                                  20

<210> SEQ ID NO 9
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 9
tttgtgtttg gagagacgag                                                  20

<210> SEQ ID NO 10
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 10
atgttcaacc ttgtcccgac t                                                21

<210> SEQ ID NO 11
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 11
taaagacggc agctatcact                                                  20

<210> SEQ ID NO 12
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 12
cccgtgattt cctccgac                                                    18

<210> SEQ ID NO 13
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 13
tcgctggttc gcttcatcg                                                   19

<210> SEQ ID NO 14
<211> LENGTH: 21
```

```
<212> TYPE: DNA
<213> ORGANISM: Artificial Sequence
<220> FEATURE:
<223> OTHER INFORMATION: The sequence is synthetized.

<400> SEQUENCE: 14
tcaaatgttc aaagccgtac a                                          21

<210> SEQ ID NO 15
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 15
aaatggcata tgggctctgt                                            20

<210> SEQ ID NO 16
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 16
cctggtggtt agcaaaaagc                                            20

<210> SEQ ID NO 17
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 17
gaaggcactg tcagctggat                                            20

<210> SEQ ID NO 18
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 18
aacgtgggaa tttctagccc                                            20

<210> SEQ ID NO 19
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 19
gttttgggcc taaacgagtg                                            20

<210> SEQ ID NO 20
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 20
```

```
catactcaac acgcaatgcc                                            20

<210> SEQ ID NO 21
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 21
tatctgcgac gacgactctg                                            20

<210> SEQ ID NO 22
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 22
agtggcctac ccgacaaagt                                            20

<210> SEQ ID NO 23
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 23
aaagcttttg ggctcctctc                                            20

<210> SEQ ID NO 24
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 24
cggaattctt cacttttggg cattgttc                                   28

<210> SEQ ID NO 25
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 25
cgggtaccct ccggagcgcc caggaagg                                   28

<210> SEQ ID NO 26
<211> LENGTH: 28
<212> TYPE: DNA
<213> ORGANISM: Artificial Sequence
<220> FEATURE:
<223> OTHER INFORMATION: The sequence is synthetized.

<400> SEQUENCE: 26
cgggtaccat gcagcagcgg cggaagtc                                   28

<210> SEQ ID NO 27
<211> LENGTH: 28
<212> TYPE: DNA
<213> ORGANISM: Artificial Sequence
```

```
<220> FEATURE:
<223> OTHER INFORMATION: The sequence is synthetized.

<400> SEQUENCE: 27 cgggatcgcct actggtcgga tgaccatg                                28

<210> SEQ ID NO 28
<211> LENGTH: 23
<212> TYPE: DNA
<213> ORGANISM: Artificial Sequence
<220> FEATURE:
<223> OTHER INFORMATION: The sequence is synthetized.

<400> SEQUENCE: 28
cctctacaac gaggacatca agt                                      23

<210> SEQ ID NO 29
<211> LENGTH: 24
<212> TYPE: DNA
<213> ORGANISM: Artificial Sequence
<220> FEATURE:
<223> OTHER INFORMATION: The sequence is synthetized.

<400> SEQUENCE: 29
cctctatcaa cgaggacatc aagt                                     24

<210> SEQ ID NO 30
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 30
cctctaaacg aggacatcaa gt                                       22
```